(12) United States Patent
Oh et al.

(10) Patent No.: US 11,097,043 B2
(45) Date of Patent: Aug. 24, 2021

(54) FILTER AND DEVICE INCLUDING THE SAME

(71) Applicant: Samsung Electronics Co., Ltd., Suwon-si (KR)

(72) Inventors: Jinho Oh, Seoul (KR); Huisung Moon, Yongin-si (KR); Minyoung Lee, Seoul (KR); Manseung Heo, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 246 days.

(21) Appl. No.: 15/999,348

(22) PCT Filed: Aug. 25, 2016

(86) PCT No.: PCT/KR2016/009445
§ 371 (c)(1),
(2) Date: Aug. 17, 2018

(87) PCT Pub. No.: WO2017/142145
PCT Pub. Date: Aug. 24, 2017

(65) Prior Publication Data
US 2019/0076593 A1    Mar. 14, 2019

(30) Foreign Application Priority Data

Feb. 17, 2016 (KR) .................. 10-2016-0018534

(51) Int. Cl.
*A61M 1/36* (2006.01)
*A61M 1/34* (2006.01)
*G01N 33/49* (2006.01)

(52) U.S. Cl.
CPC ............ *A61M 1/3633* (2013.01); *A61M 1/34* (2013.01); *G01N 33/491* (2013.01); *A61M 2202/0429* (2013.01); *A61M 2202/0439* (2013.01)

(58) Field of Classification Search
CPC .................. A61M 1/3633; A61M 1/34; A61M 2202/0429; A61M 2202/0439; G01N 33/491
See application file for complete search history.

(56) References Cited

U.S. PATENT DOCUMENTS 5,476,587 A    12/1995  Kuroki et al.
5,753,014 A *  5/1998   Van Rijn ............ B01D 67/0072
                                                      96/12

(Continued)

FOREIGN PATENT DOCUMENTS

EP       1666129 A1      6/2006
JP       2001-188066 A   7/2001

(Continued)

OTHER PUBLICATIONS

Alderson, Andrew, et. al., An auxetic filter: a tunable filter displaying enhanced size selectivity or defouling properties. 2000, Industrial & Engineering Chemistry Research (Year: 2000).*

(Continued)

*Primary Examiner* — Bradley R Spies
*Assistant Examiner* — Jeannie McDermott
(74) *Attorney, Agent, or Firm* — Leydig, Voit & Mayer, Ltd.

(57) ABSTRACT

A filter and a device including the filter may include a filter and a plurality of pores arranged two-dimensionally on the filter. The plurality of pores may include a plurality of first pores having a longer structure in a certain direction and a plurality of second pores having a longer structure in a direction different from that of the first pore. The first and second pores may have a two-dimensional arrangement in order to suppress or prevent the occurrence of cracks in the filter due to stress.

17 Claims, 18 Drawing Sheets

(56) References Cited

U.S. PATENT DOCUMENTS

| | | | |
|---|---|---|---|
| 6,491,819 B2 * | 12/2002 | Prince | A61M 1/34 |
| | | | 210/321.67 |
| 6,497,821 B1 | 12/2002 | Bellamy, Jr. et al. | |
| 6,811,753 B2 | 11/2004 | Hirao et al. | |
| 8,557,341 B2 * | 10/2013 | Yang | B82Y 10/00 |
| | | | 427/271 |
| 2002/0033367 A1 * | 3/2002 | Prince | A61M 1/265 |
| | | | 210/650 |
| 2003/0130718 A1 | 7/2003 | Palmas et al. | |
| 2011/0059291 A1 * | 3/2011 | Boyce | C08J 5/18 |
| | | | 428/136 |
| 2011/0100921 A1 | 5/2011 | Heinrich | |
| 2012/0178097 A1 * | 7/2012 | Tai | G01N 33/5011 |
| | | | 435/7.1 |
| 2013/0214875 A1 * | 8/2013 | Duncan | B82Y 30/00 |
| | | | 333/186 |
| 2014/0190888 A1 | 7/2014 | Van Rijn et al. | |
| 2016/0252436 A1 | 9/2016 | Jeon et al. | |
| 2017/0247662 A1 * | 8/2017 | Kanbara | G03F 7/038 |

FOREIGN PATENT DOCUMENTS

| | | |
|---|---|---|
| JP | 2013-042689 A | 3/2013 |
| KR | 1999-0071591 A | 12/2002 |
| KR | 2012-0042533 A | 5/2012 |
| KR | 2015-0020290 A | 8/2017 |

OTHER PUBLICATIONS

Korean Intellectual Property Office, International Search Report in International Application No. PCT/KR2016/009445 (dated Nov. 29, 2016).

* cited by examiner

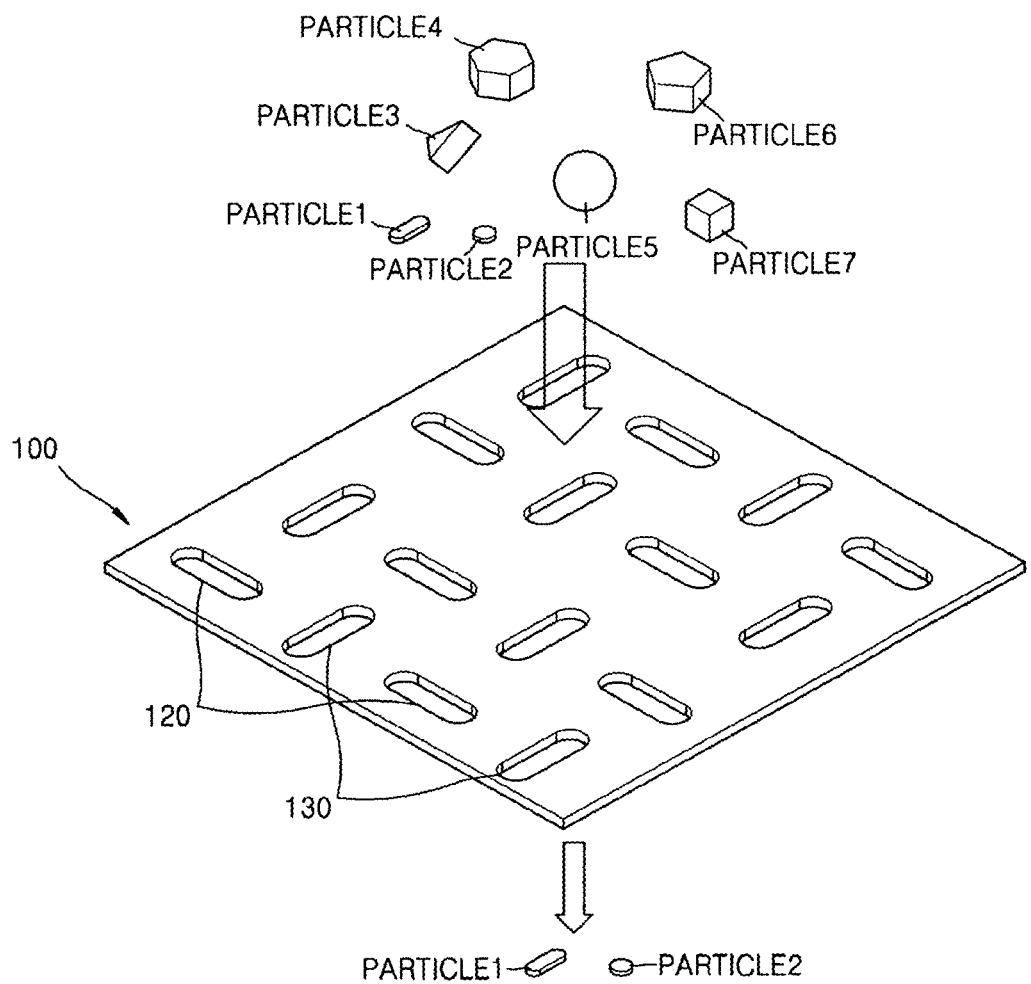
[Figure 1]

[Figure 2]
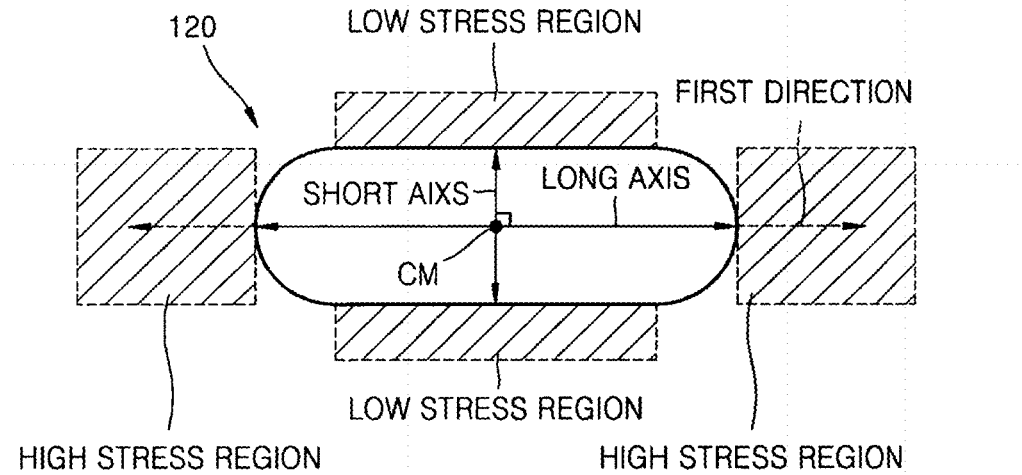
[Figure 3]
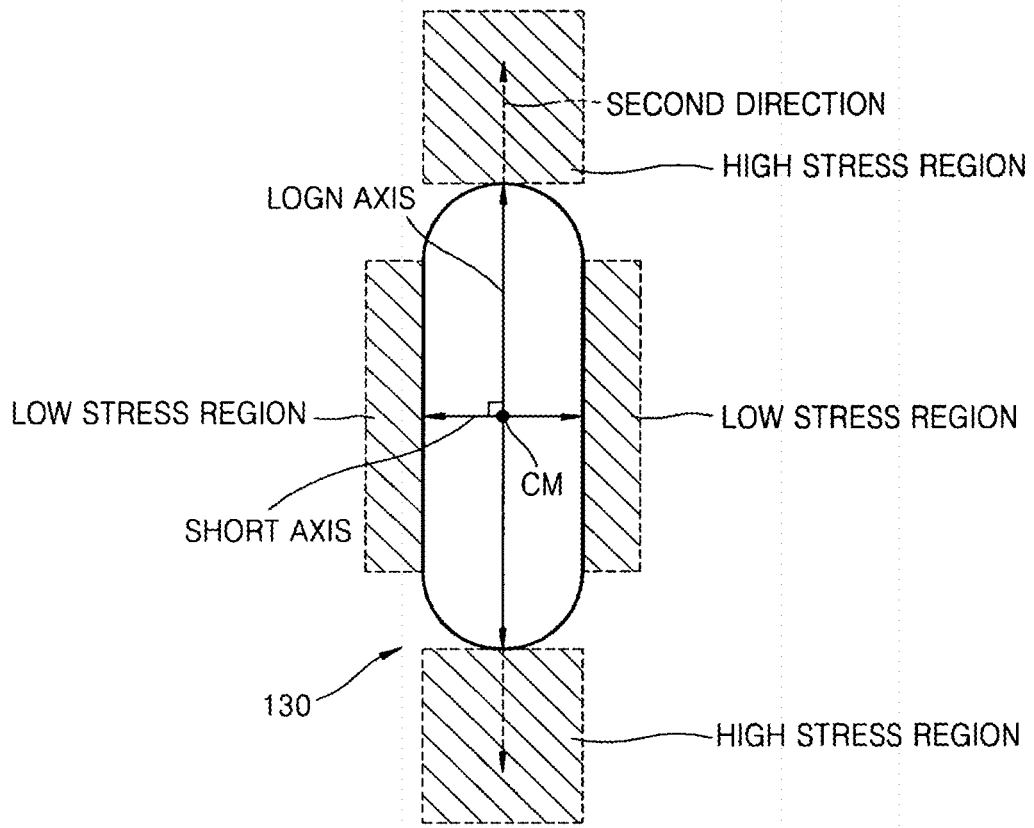

[Figure 4]
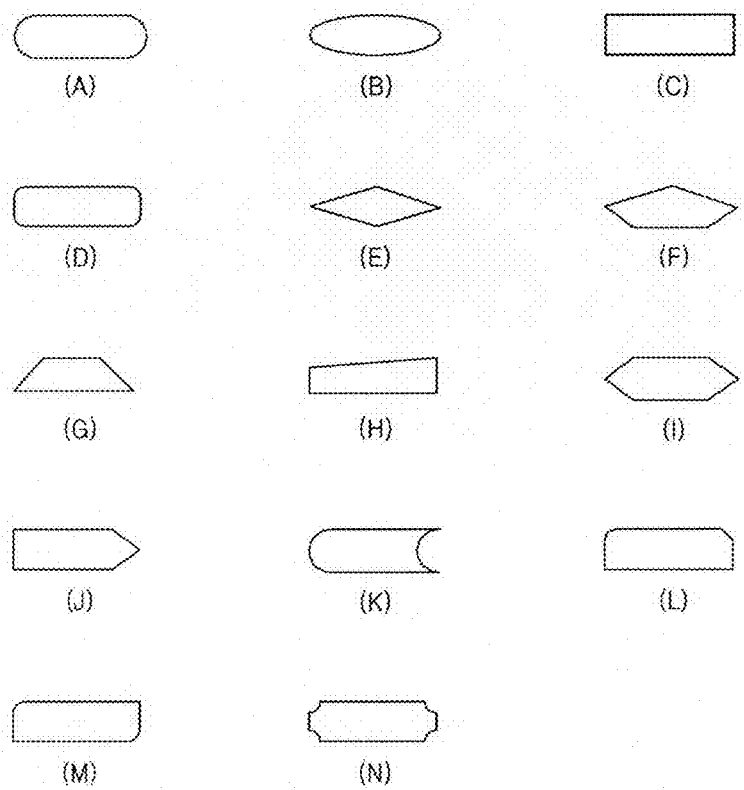
[Figure 5]

[Figure 6]
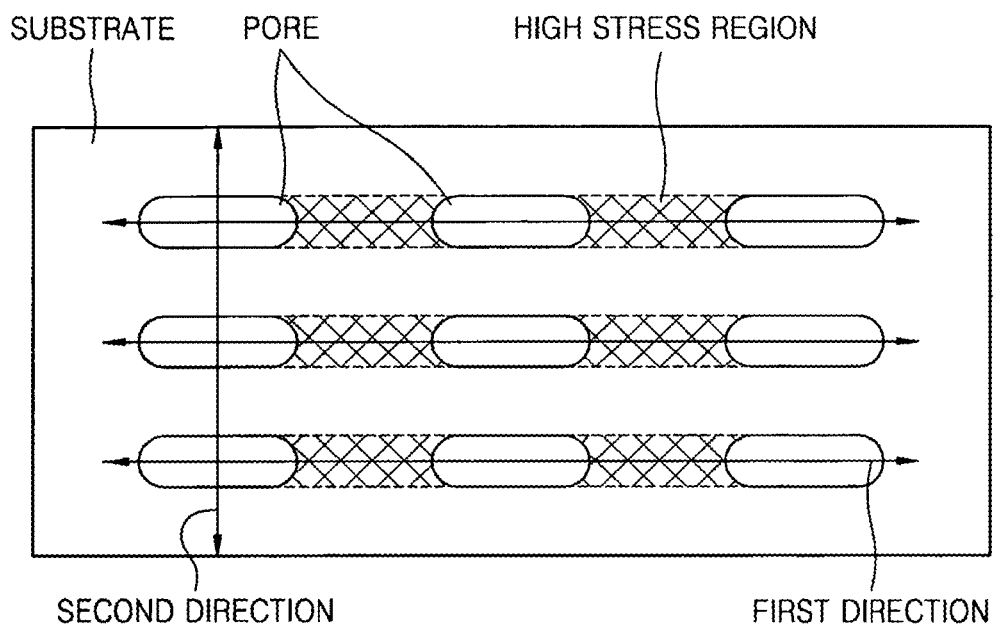

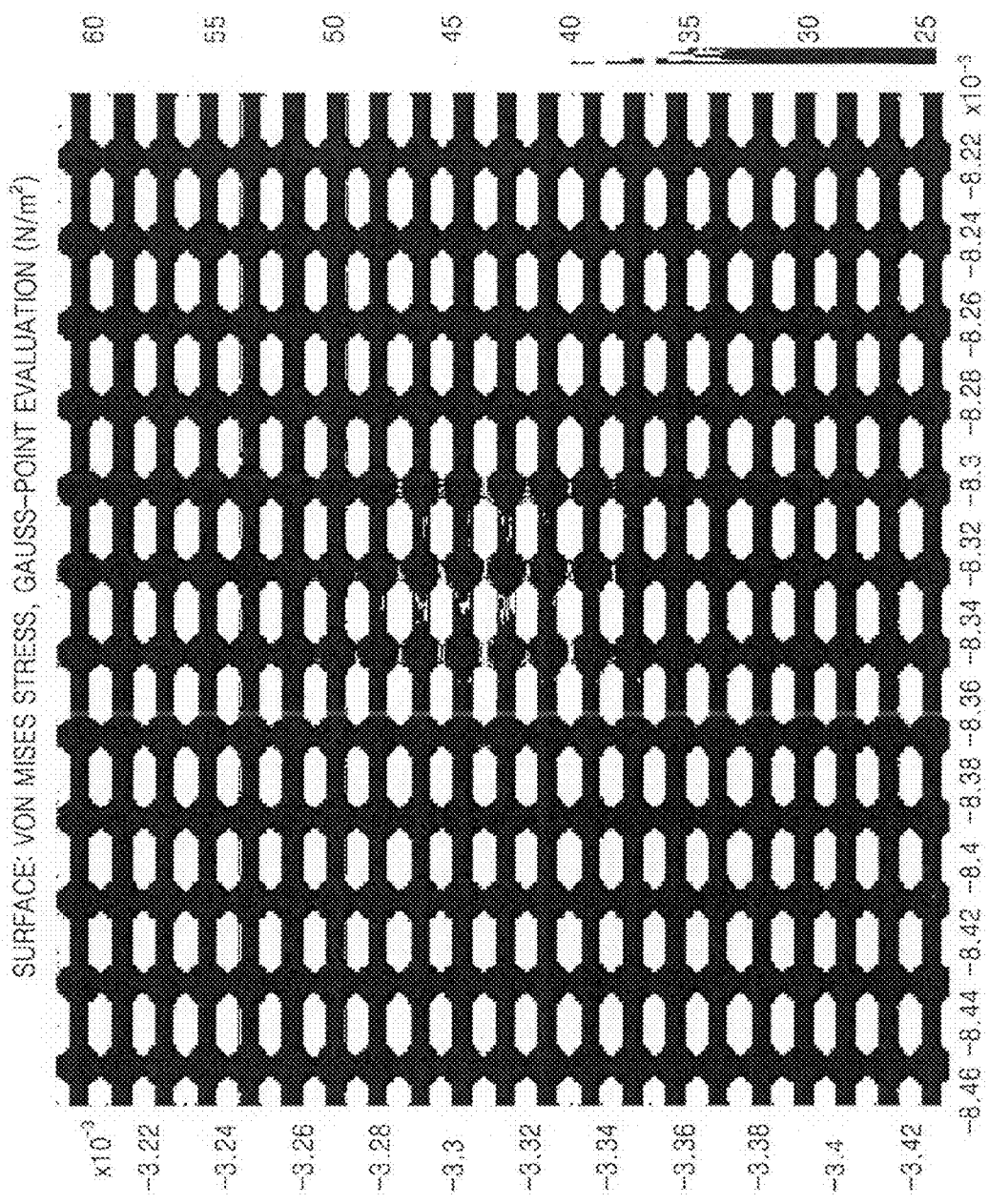
[Figure 7]

[Figure 8]
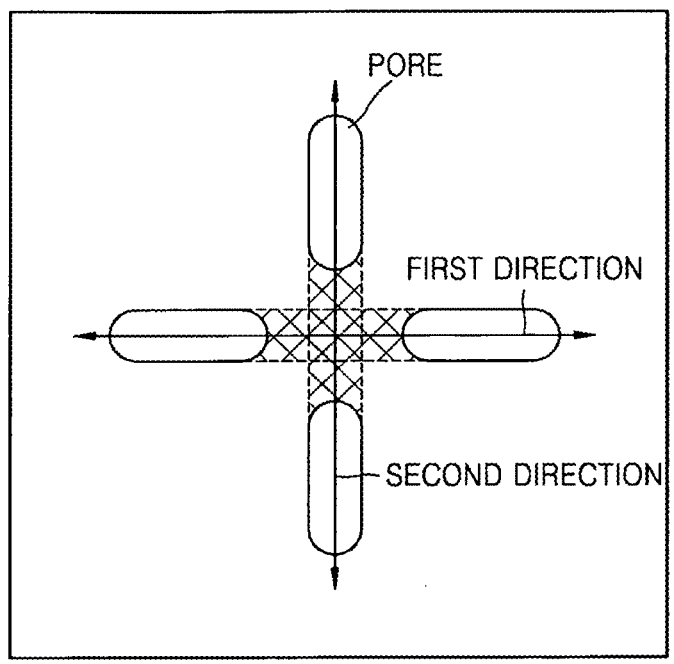

[Figure 9]
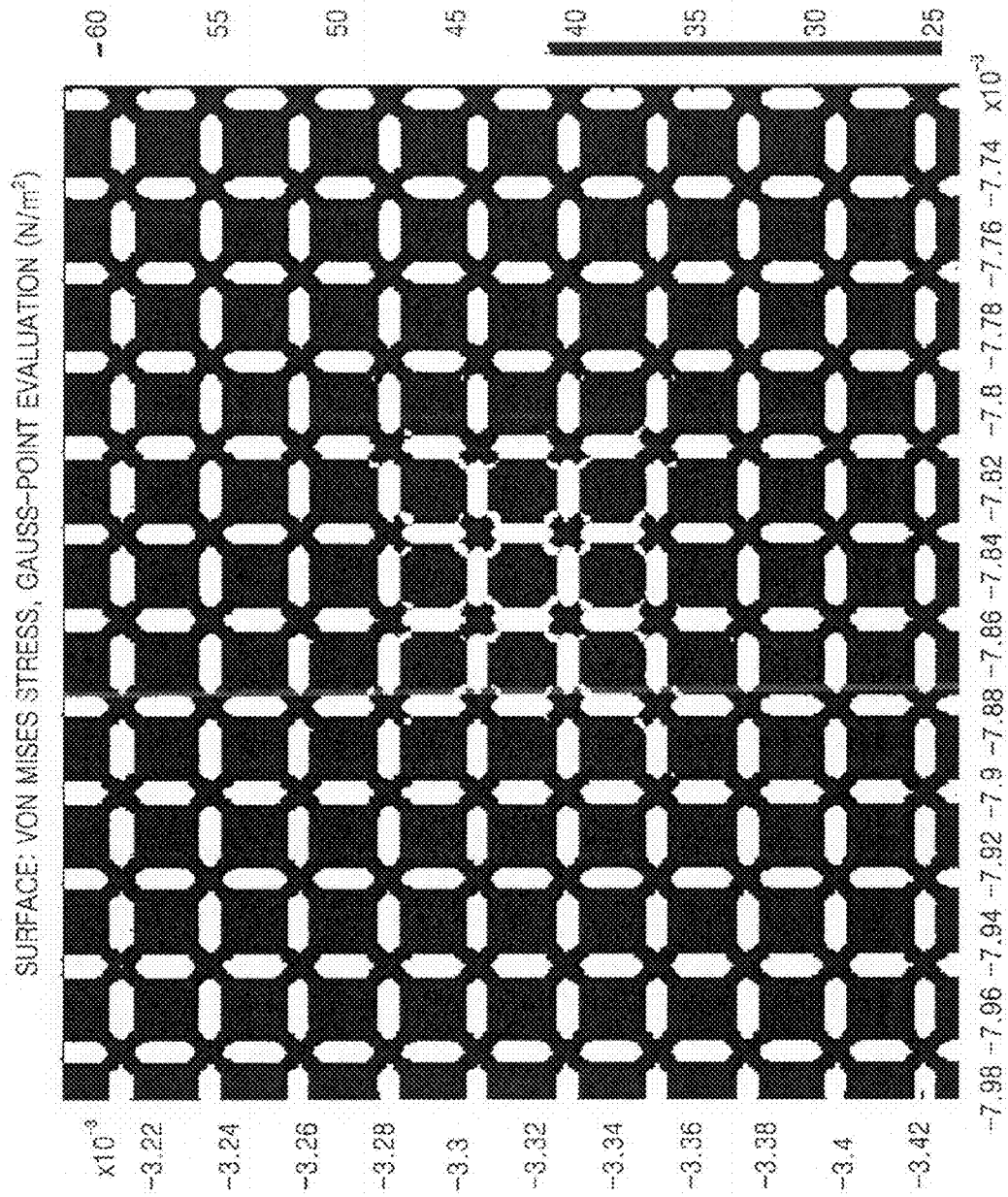

[Figure 10]
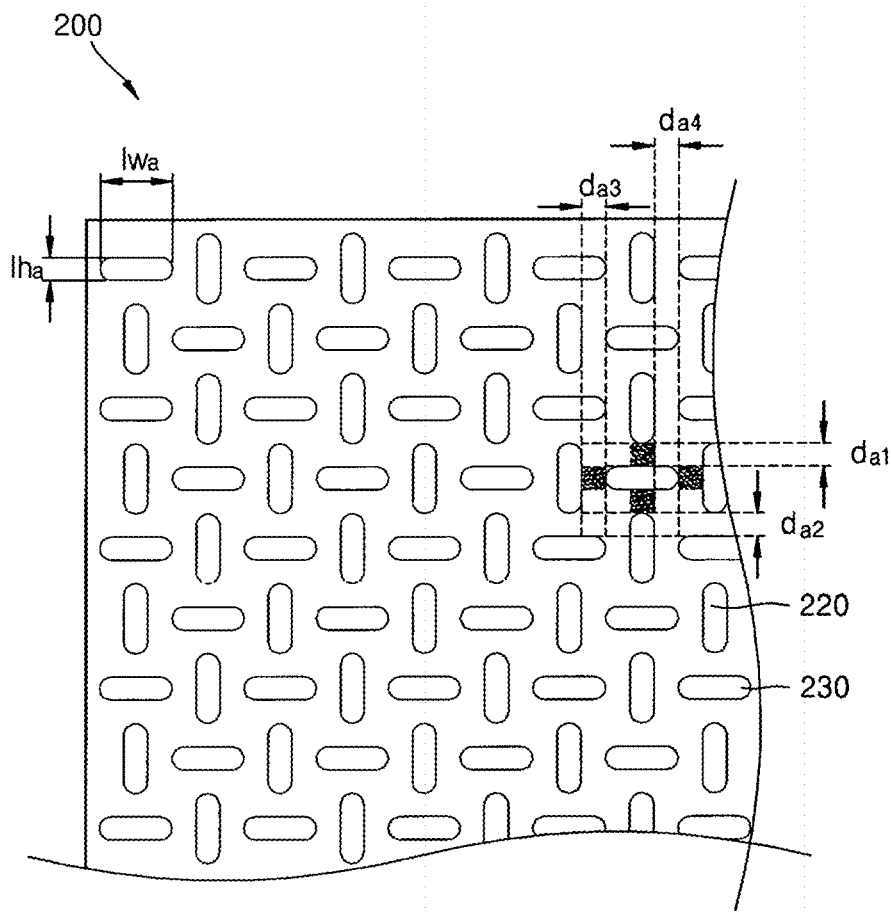

[Figure 11]
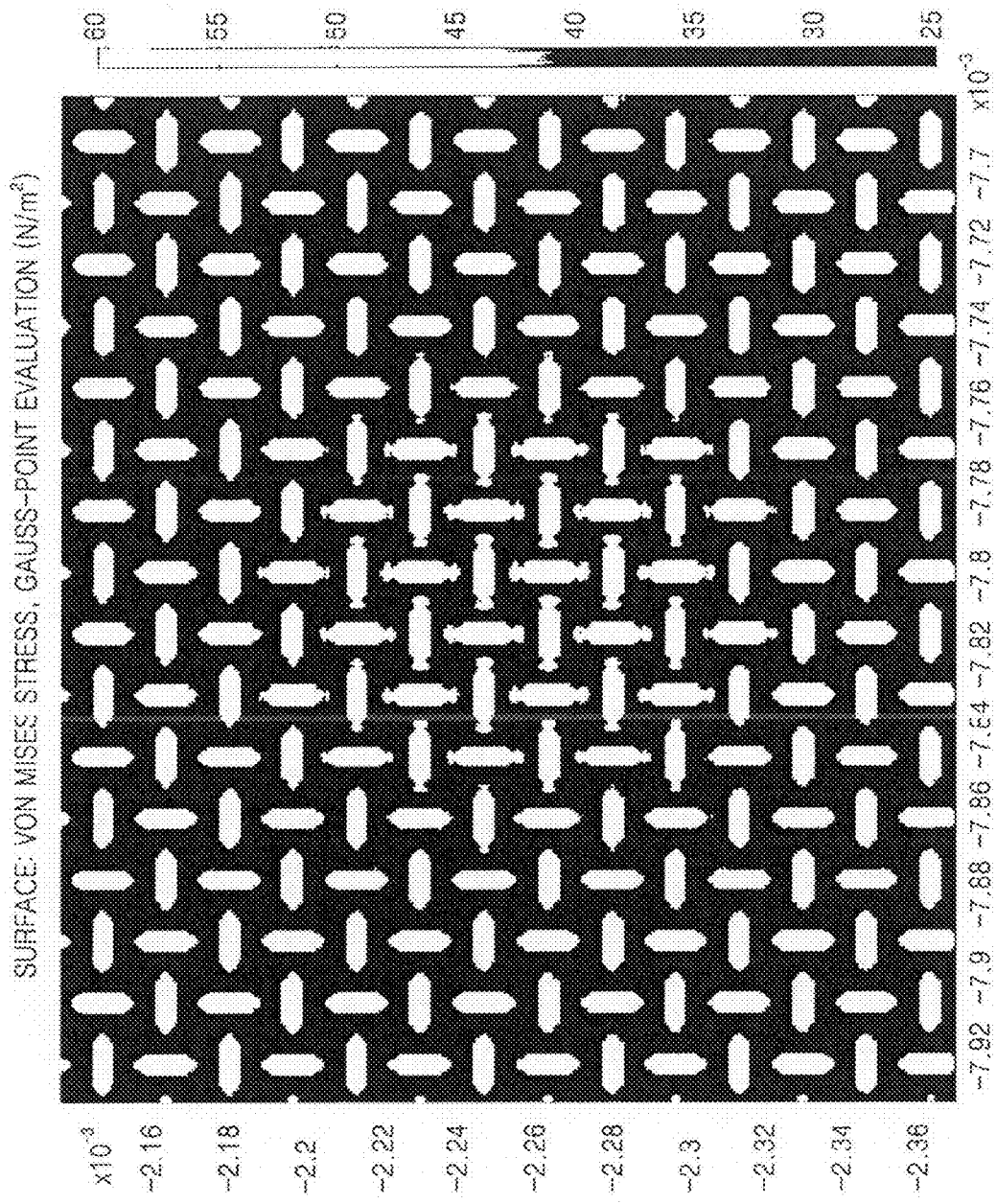

[Figure 12]
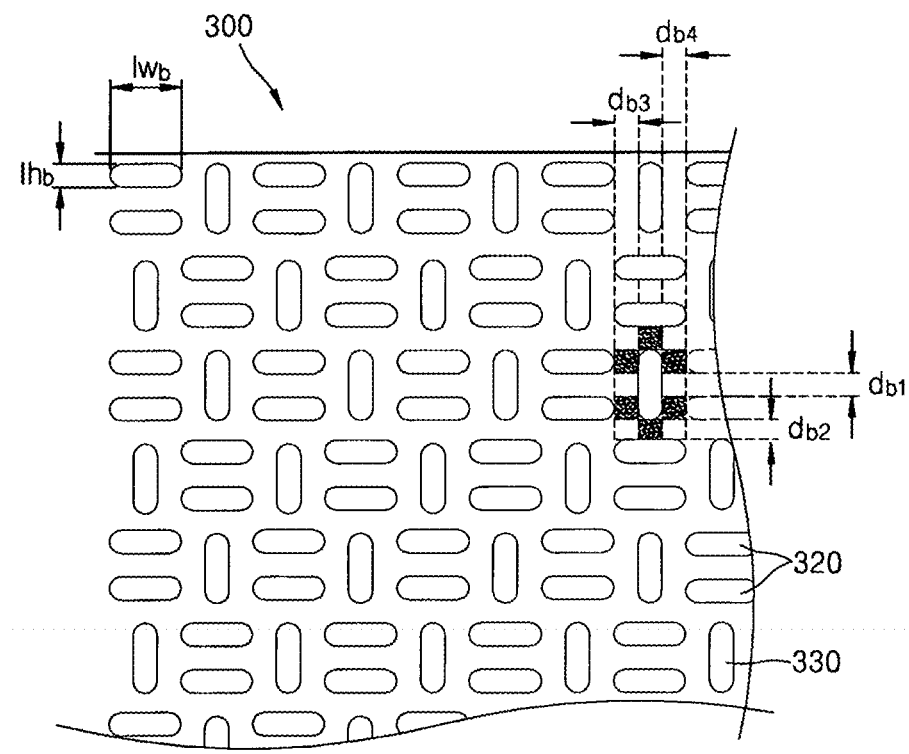

[Figure 13]
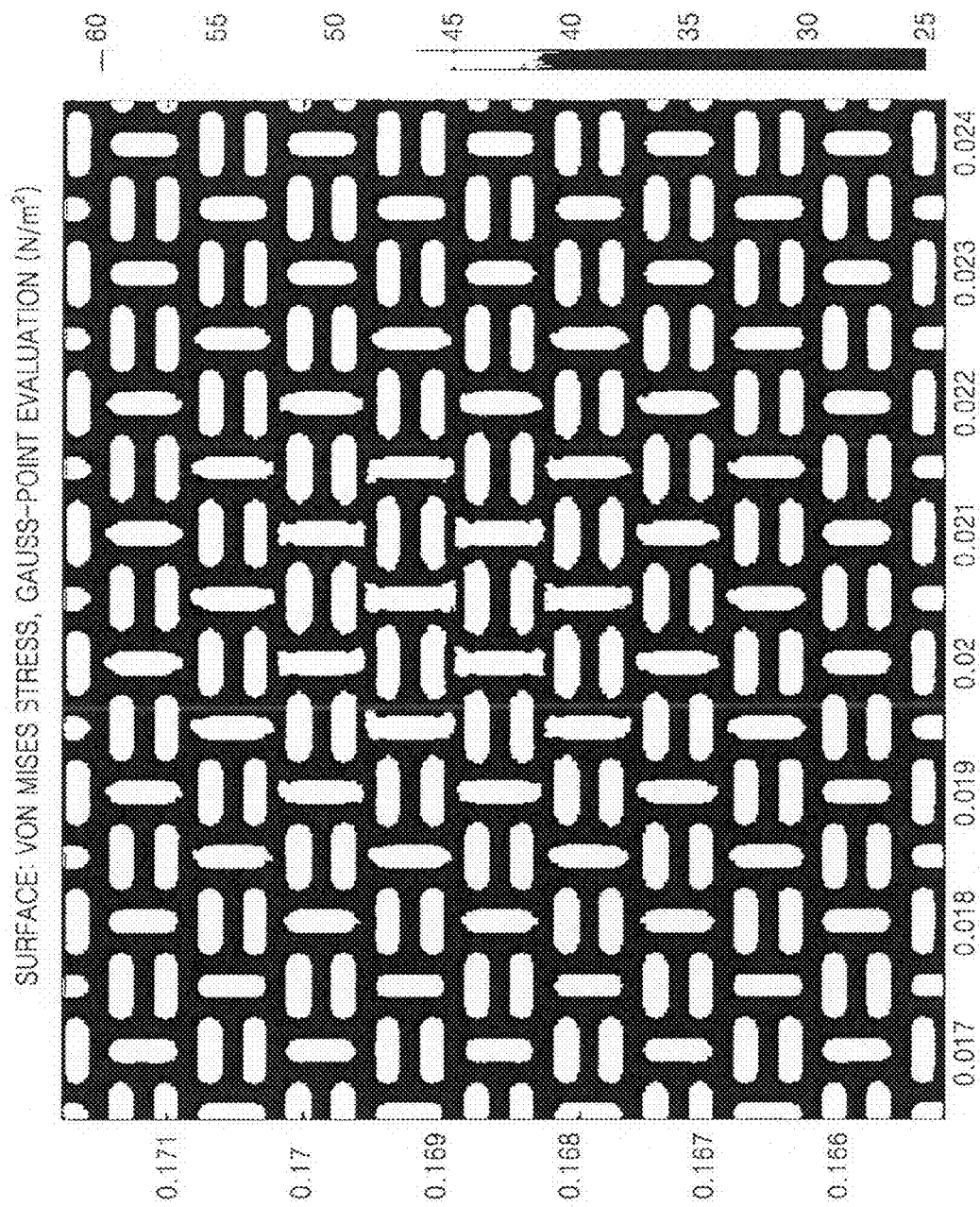

[Figure 14]
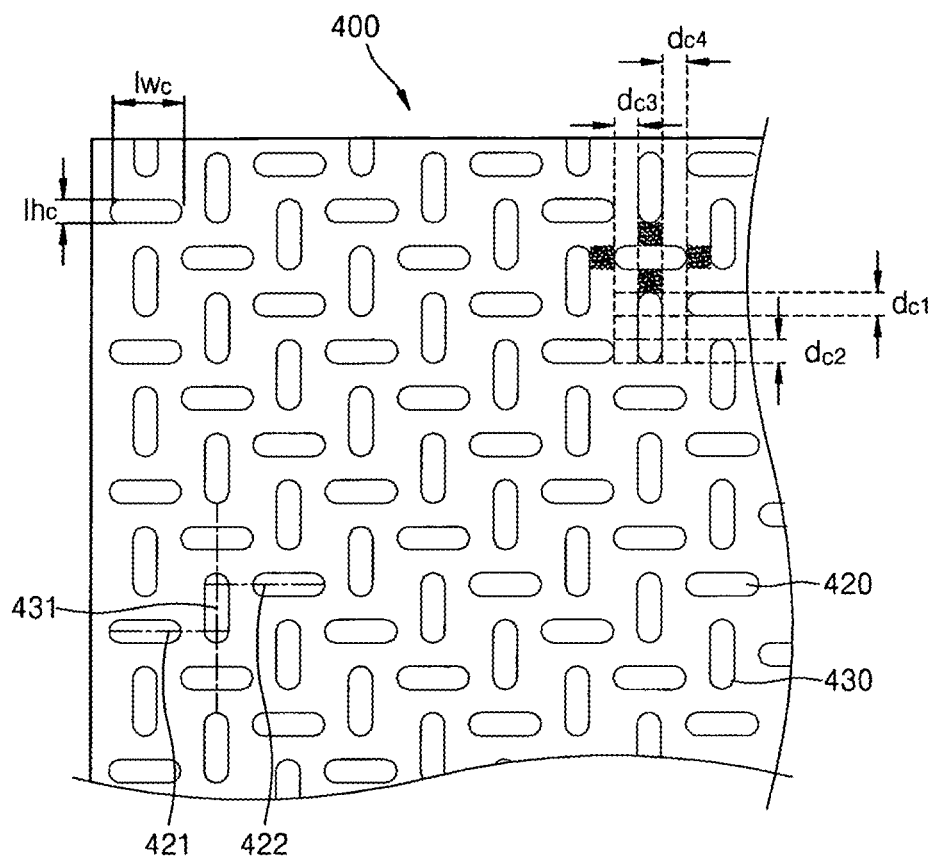

[Figure 15]
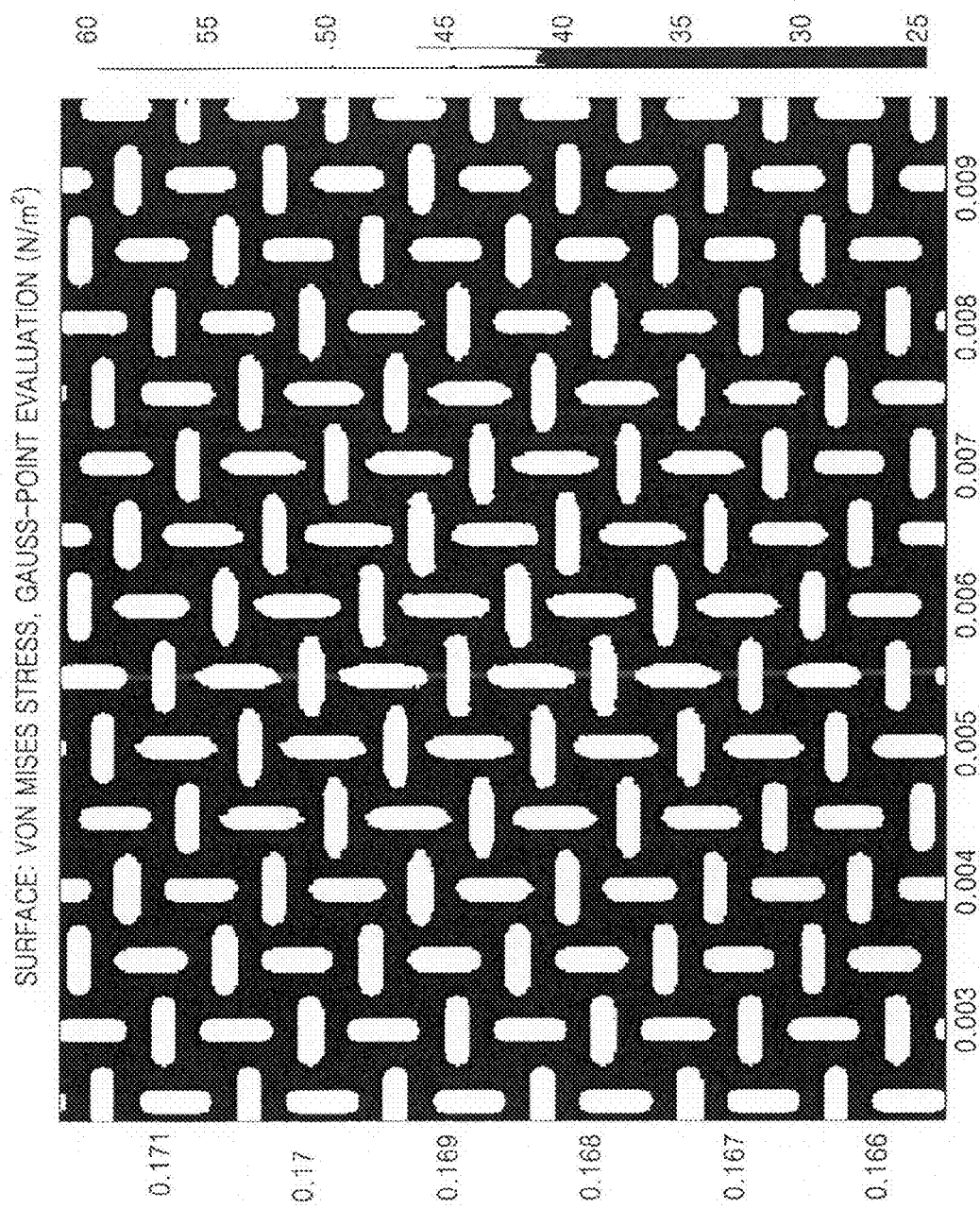

[Figure 16]
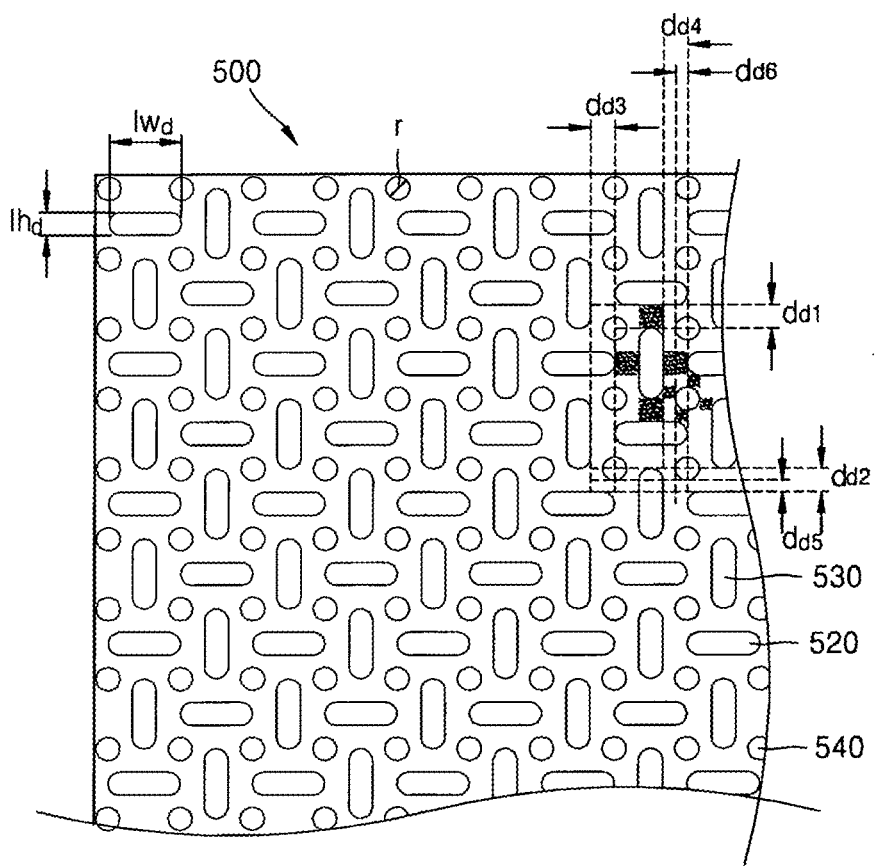

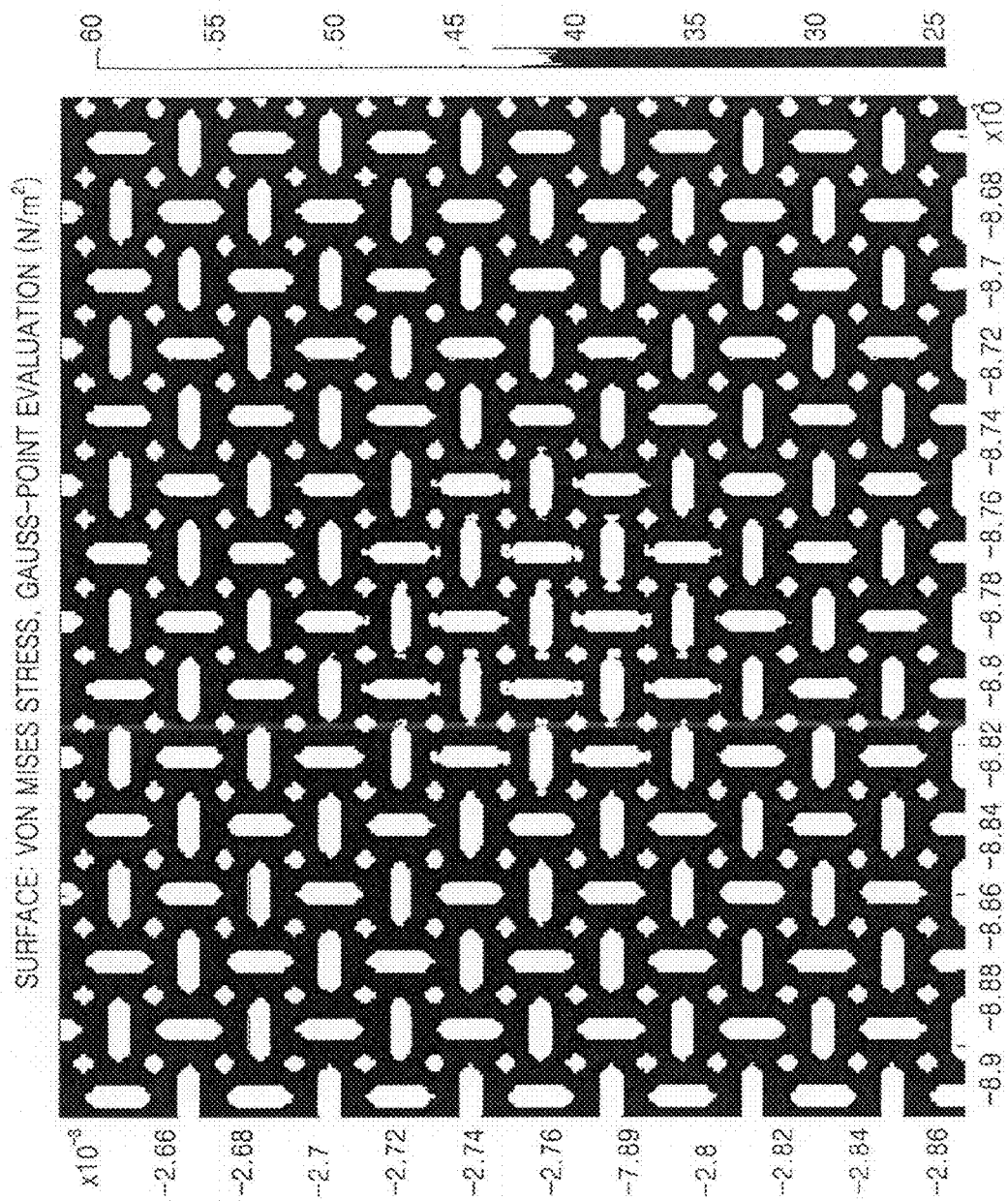
[Figure 17]

[Figure 18]
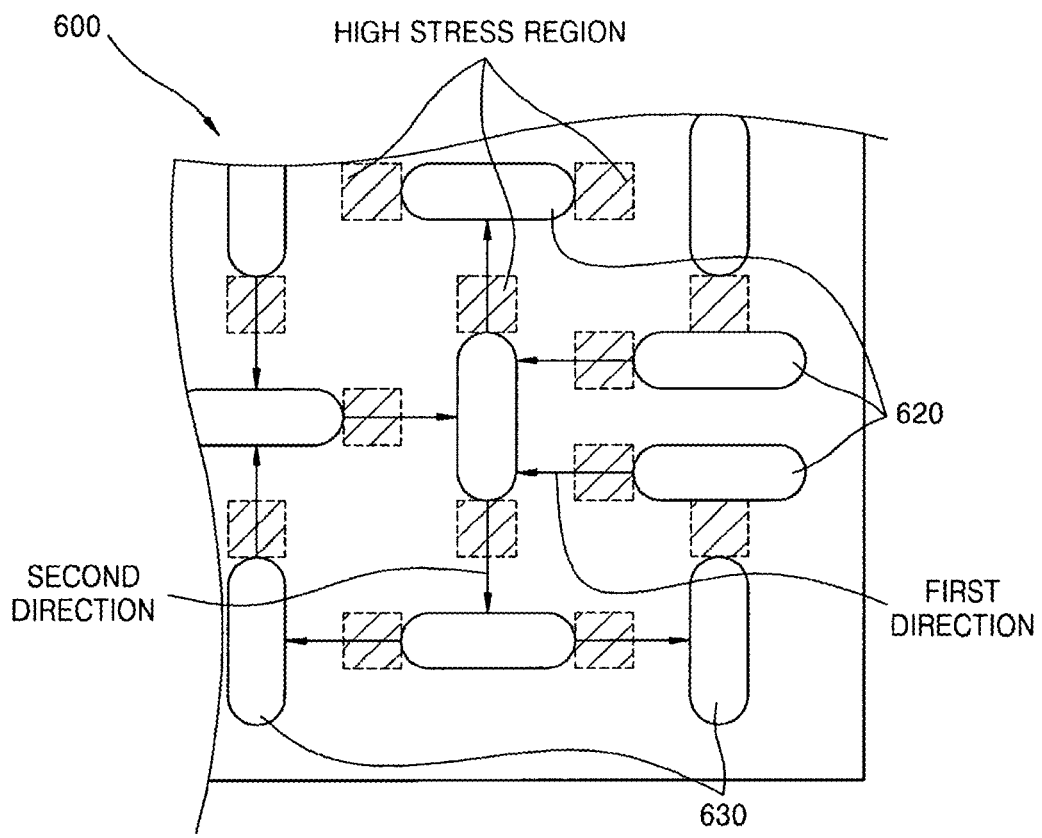

[Figure 19a]
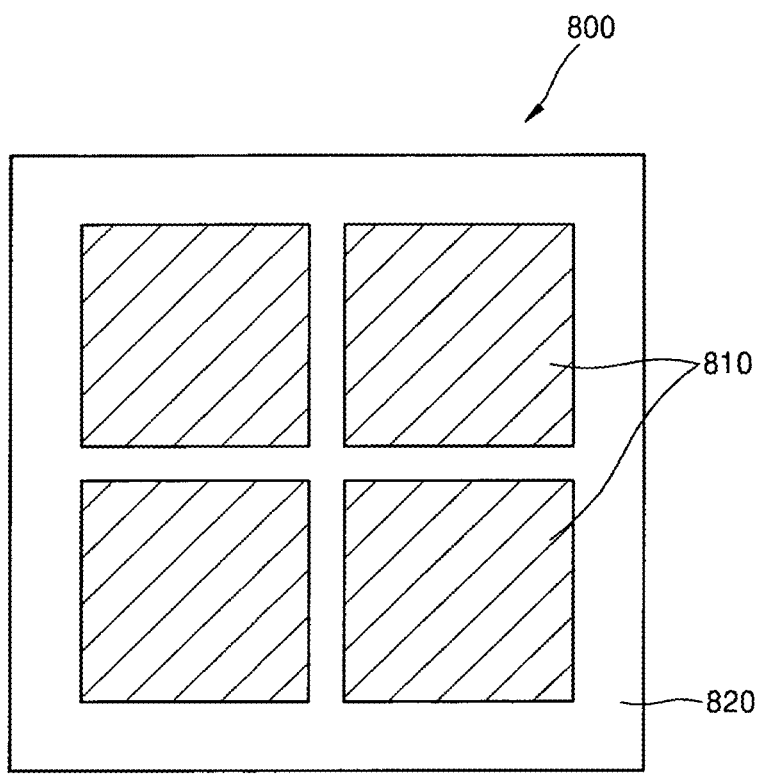
[Figure 19b]
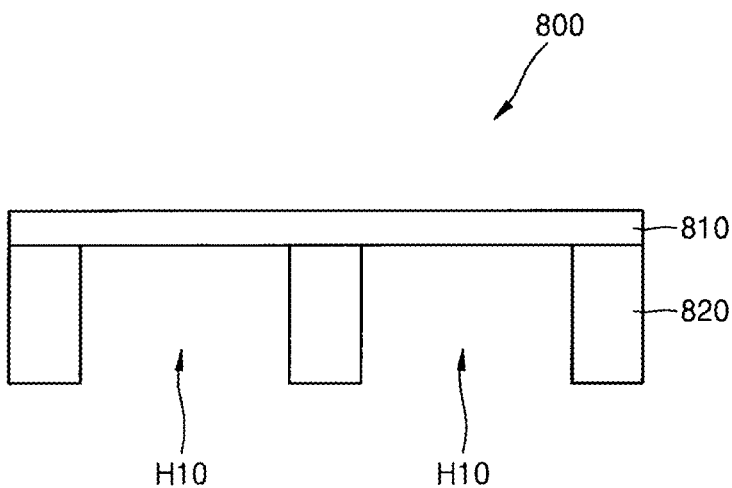

[Figure 20]
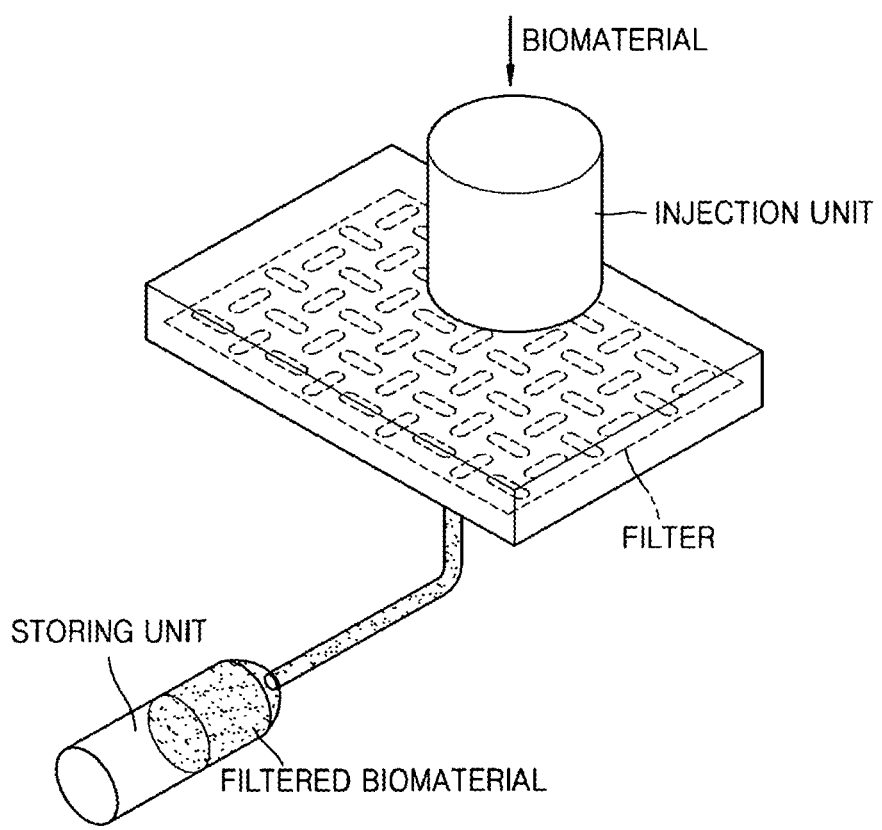

FILTER AND DEVICE INCLUDING THE SAME

TECHNICAL FIELD

The present disclosure relates to a filter and a device including the filter.

BACKGROUND ART

Various devices and methods may be utilized for filtering biomaterials. Especially, research has been performed on devices to separate leukocytes from remaining globule cells in the blood. The separated leukocytes may be used in various treatment processes including an autologous cytotherapy. Conventional leukocyte separation methods needed for a cell therapy, etc. have difficulties in separating leukocytes fast from the blood, which has a volume of more than or equal to about 10 ml.

For example, a chemical red blood cell lysis, which is a method using characteristic differences of cell membranes, may selectively separate red blood cells via a neutral solution (PH 7). However, leukocytes may be contaminated by remains of dissolved red blood cells. A density-based separation method may be used to separate a red blood cell layer and a leukocyte layer via a density difference by using a solution having a certain density such as Ficoll-Paque. However, this method is time consuming and requires a high competency level of the personnel using it. A track-etched membrane filter may have a non-uniform distribution of pores and a low pore density, and thus, may not be suitable for mass separation of red blood cells.

DISCLOSURE

Technical Problem

Provided is a filter with good filtering properties and a device including the same. The filter may prevent the occurrence of cracks therein while maintaining a relatively fast filtering speed.

Technical Solution

According to an aspect of an embodiment, the filter may include a plurality of pores two-dimensionally arranged, and may be configured to filter a biomaterial via the plurality of pores.

The plurality of pores may include a plurality of first pores extending in a first direction and having a relatively longish structure in the first direction than in a direction perpendicular to the first direction; and a plurality of second pores having a relatively longish structure in a second direction different from the first direction, in which an end portion along a major axis direction of the second pore may face a central portion of a longer side of the first pore.

Advantageous Effects

A filter and a device including the same according to the present disclosure may have an arrangement shape of pores capable of preventing an extension of cracks and also may have a high filtering speed due to a high density of pores.

In addition, the filter and the device including the same according to the present disclosure may be implemented to have high reproducibility irrespective of skill of a measurer.

In addition, the filter and the device including the same according to the present disclosure may prevent damage on cells.

In addition, since a general semiconductor process can be utilized in manufacturing the filter, the manufacturing of the filter may be easy and a cost thereof may be reduced.

DESCRIPTION OF DRAWINGS

FIG. 1 is a perspective view of a filter according to an embodiment.

FIG. 2 is a plan view of a first pore.

FIG. 3 is a plan view of a second pore.

FIG. 4 is a diagram illustrating a red blood cell and kinds and sizes of a leukocyte.

FIG. 5 is a diagram illustrating various shapes of pores.

FIG. 6 is a plan view of a filter according to a first comparative embodiment.

FIG. 7 is a diagram illustrating a stress simulation result with regard to the filter of FIG. 6.

FIG. 8 is a plan view of a filter according to a second comparative embodiment.

FIG. 9 is a diagram illustrating a stress simulation result with regard to the filter of FIG. 8.

FIG. 10 is a plan view of a filer according to an embodiment.

FIG. 11 is a diagram illustrating a stress stimulation result with regard to the filter of FIG. 10.

FIG. 12 is a plan view of a filer according to an embodiment.

FIG. 13 is a diagram illustrating a stress simulation result with regard to the filter of FIG. 12.

FIG. 14 is a plan view of a filter according to another embodiment.

FIG. 15 is a diagram illustrating a stress simulation result with regard to the filter of FIG. 14.

FIG. 16 is a plan view of a filter according to another embodiment.

FIG. 17 is a diagram illustrating a stress simulation result with regard to the filter of FIG. 16.

FIG. 18 is a plan view of a filter according to another embodiment.

FIGS. 19A and 19B are diagrams illustrating a filter structure according to an embodiment.

FIG. 20 is a photo of a device including a filter according to an embodiment described above.

BEST MODE

According to an aspect of an embodiment, the filter may include a plurality of pores two-dimensionally arranged, and may be configured to filter a biomaterial via the plurality of pores.

The plurality of pores may include a plurality of first pores extending in a first direction and having a relatively longish structure in the first direction than in a direction perpendicular to the first direction; and a plurality of second pores having a relatively longish structure in a second direction different from the first direction, in which an end portion along a major axis direction of the second pore may face a central portion of a longer side of the first pore.

The first and second pores may be alternately arranged, respectively in the first and second directions.

The end portion along the major axis direction of the first pore may face the central portion of the longer side of the second pore or an area adjacent thereto.

A pair of first pores may be respectively arranged on one side and the other side along the first direction of the second pore, and a pair of first pores may be respectively arranged on one side and the other side along the second direction of the second pore.

Each one of first pores may be arranged on the one side and the other side along the first direction of the second pore, and a center line in the major axis direction of the first pore on the one side and the center line in the major axis direction of the first pore on the other side may be separated from each other in the second direction.

The plurality of pores may further include a plurality of third pores between the plurality of first pores and the plurality of second pores.

The third pore may have same lengths in the first and second directions.

The plurality of pores may have uniform gaps in the first and second directions.

The first and second pores may have elliptical shapes.

The first and second pores may respectively have a ratio of a length in the major axis direction over that in the minor axis direction as more than or equal to about 2.5.

The first and second pores may respectively have the length in the major axis of about 10 µm to about 20 µm, and that in the minor axis direction of about 4 µm to about 7 µm.

A shortest distance between the first pore and the second pore may be about 4 µm to about 7 µm.

The area ratio which the plurality of pores occupy on a filter area with the plurality of pores distributed thereon may be more than or equal to about 30%.

The filter may have a plate structure.

The filter may include a semiconductor material.

The filter may include a rigid material including inorganic substance.

The biomaterial may include the blood, and the first and second pores may be configured to allow a red blood cell of the blood to pass therethrough but not to allow a white blood cell to pass therethrough.

A support member may be arranged on a bottom surface of the filter to support it and may include at least one of openings which expose the bottom surface of the filter.

According to another aspect of an embodiment, a filter may include a plurality of pores that are two-dimensionally arranged and may be configured to filter the biomaterial by using the plurality of pores, in which the plurality of pores include: a plurality of first pores extending in a first direction and having a relatively longish structure in the first direction than in a direction perpendicular to the first direction; and a plurality of second pores having a relatively longish structure in a second direction different from the first direction, in which the first and second pores may be alternately arranged, respectively in the first and second directions.

An end portion along a major axis direction of the first pore may face a central portion of a longer side of the second pore.

The end portion along the major axis direction of the second pore may face the central portion of the longer side of the first pore.

According to another aspect of an embodiment, a device may include a filter according to descriptions above; an injection unit injecting the biomaterial into the filter; and a storing unit storing the biomaterial which has passed through the filter.

MODE FOR INVENTION

A filter and a device including the same will be described in detail below with reference to the appended diagrams. Layers, widths, and thickness of regions illustrated in the diagrams may be exaggerated for clarity and convenience of explanation. Throughout the description, like reference numerals denote like components.

Although general terms that are currently widely used are selected as the terms used in the present disclosure while considering functions of the components in the embodiments, selection of the terms may vary depending on the intention of those skilled in the art, judicial precedents, emergence of new technology, etc. In addition, in certain cases, there may be terms arbitrarily chosen by the applicant and the meanings of the terms shall be stated in detail in the descriptions of the corresponding embodiments. Therefore, the terms used in an embodiment should be defined based, not on the names of a simple term, but on the meaning of the terms and the contents throughout the embodiment.

Throughout the specification, when a portion "includes" an element, another element may be further included in the portion, rather than excluding the existence of the other element, unless otherwise described.

FIG. 1 is a perspective view of a filter 100 according to an embodiment. FIG. 2 is a plan view of a first pore 120. FIG. 3 is a plan view of a second pore 130. FIG. 4 is a diagram illustrating a red blood cell and kinds and sizes of a leukocyte. FIG. 5 is a diagram illustrating various shapes of pores.

Referring to FIG. 1, the filter 100 may include a plurality of pores 120 and 130 arranged two-dimensionally and may be configured to filter a biomaterial via the plurality of pores 120 and 130.

The filter 100 may have a plate structure and may include a semiconductor material. For example, the filter 100 may include a semiconductor material including group 4 elements such as silicon (Si). When the filter 100 is manufactured from a semiconductor material, pores 120 and 130 may be formed by a conventional semiconductor process. For example, the pores 120 and 130 of the filter 100 may be formed by using a photo lithography process. In this case, the filter 10 may be relatively inexpensive and suitable for mass production.

The semiconductor material used in the semiconductor process is a brittle material having a very low elasticity, and thus, a crack may easily occur in the filter 100. The crack generated by a brittle fracture may propagate to an area adjacent to the filter 100. According to an embodiment, propagation of a crack in the filter 100 due to a brittle fracture may be prevented by an array of the pores 120 and 130.

Table 1 illustrates general values of Young's modulus and fracture toughness of several materials including monocrystalline silicon, which is widely used in an electronic phototype process, etc.

TABLE 1

| Material | Young's modulus [GPa] | Fracture toughness [MPa · m$^{1/2}$] |
|---|---|---|
| Monocrystalline silicon | 131 | 0.83~0.95 |
| Diamond | 1000 | 3.4 |
| Concrete | 400 | 0.2~1.4 |
| Steel | 200 | 50~100 |
| Glass | 65 | 0.7~0.8 |
| Nylon | 5 | 2.5~3.0 |
| Polystyrene (PS) | 2.28~3.28 | 0.7~1.1 |
| Dentin | 18.6 | 3.1 |
| Smooth muscle | 0.000006 | — |

Referring to Table 1, the Young's modulus of silicon, which is used to manufacture the filter 100, is 131 GPA. Silicon has little plastic deformation to an external pressure and fracture toughness similar to that of glass. Thus, when stress on the filter 100 exceeds a certain limit, the surface of the filter 100, instead of being curved, may be broken from the pores 120 and 130 which are physically most vulnerable due to brittle destruction and from other boundary areas between components, and cracks may occur. The filter 100 may minimize damage in filtering capacity thereof via an array of the pores 120 and 130 according to an embodiment.

When the filter 100 is thin, the filtering performance may be improved. When the filter 100 is too thick, particles may not pass therethrough and remain stuck in the pores 120 and 130. Since an aspect ratio affects manufacturing of a semiconductor structure in a photo lithography process, when lengths of the pores 120 and 130 are several microns, an overall thickness of the filter 100 may be limited to a level of dozens of microns in order to perform a fine process. However, the overall thickness is not necessarily limited thereto. For example, the thickness of the filter 100 may be several times greater than the length in the minor axis direction of the pores 120 and 130. For example, the thickness of the filter 100 may be greater than several microns or dozens of microns. As an example, the thickness of the filter 100 may be approximately about 50 μm.

The pores 120 and 130 may include a plurality of first pores 120 and a plurality of second pores 130. The pores 120 and 130 may denote holes which are two-dimensionally arranged on the filter 100. A cross-sectional shape and a length component of the pores 120 and 130 may be determining factors of whether particles may pass therethrough. Referring to FIG. 1, among particles 1 through 7, only particles 1 and 2, which have smaller cross-sections than the pores 120 and 130, may pass through the filter 100 and other particles 3 through 7 may not pass through the filter 100.

Referring to FIG. 2, the first pore 120 may be a pore having a relatively longish shape along a first direction. The first pore 120 may have the length of the major axis along the first direction larger than that of the minor axis in a direction perpendicular to the first direction. Such a shape of the first pore 120 may increase a ratio of an area over the number thereof, and enhance filtering efficiency of the filter 100. For example, a ratio of the length along the major axis direction over that along the minor axis direction of the first pore 120 may be more than or equal to about 2.5. A crossing point of the major axis and the minor axis of the first pore 120 may be a central point of the first pore 120. The central point may correspond to a center of mass (CM). Since the pore is a hollow hole with zero mass, the CM thereof presupposes that the density of the pore is uniform.

Referring to FIG. 3, the second pore 130 may be a pore having a relatively longish shape along a second direction. The second pore 130 may have the length of the major axis along the second direction larger than that of the minor axis in a direction perpendicular to the second direction. For example, a ratio of the length along the major axis direction over that along the minor axis direction of the second pore 130 may be more than or equal to about 2.5.

The crossing point of the major axis and the minor axis of the second pore 130 may be the CM of the second pore 130.

The first direction and the second direction may be different directions from each other. For example, the first direction may have a certain angle from the second direction. For example, the first direction may be perpendicular to the second direction.

Due to a longish structure of the first and second pores 120 and 130, a high stress region and a low stress region, which are relatively divided, may be formed on the filter 100. Descriptions will be provided for the first pore 120 as an example for the sake of convenience and descriptions below may be applicable to the second pore 130 also.

A stress region may denote an area on the filter 100 except pores to which pressure is applied during a filtering process of particles or liquid. There is no stress region on the filter 100 when particles or liquid are not applied to the filter 100. During the filtering process of particles or liquid, pressure may be applied to the filter 100 via an accumulation of particles or liquid thereon. The area on the filter 100 to which pressure is applied may be defined as the stress region. The stress region may be divided into the high stress region having a high level of stress and the low stress region having a low level of stress. The stress region may vary depending on not only an amount of particles or liquid during the filtering process but also sizes and shapes of the pores arranged on the filter 100. For example, as the level of stress of the stress region increases, cracks may easily occur in the corresponding stress region during the filtering process.

The stress region may be differently formed depending on the shape of the pore, and material and the thickness of the filter 100. For example, when the pore arranged on the filter 100 is isotropic or circular, the stress region may be uniformly formed along the circumference of a circle. Isotropic pores may have uniform stress regions on the filter 100 regardless of an arrangement shape of pores. However, a filter with isotropic pores arranged thereon may have a lower pore density than that with longish pores arranged thereon and thus, a filtering speed may be relatively low. The pore density is a ratio of an area of the plurality of pores over the filter area with the plurality of pores distributed thereon.

The first pore 120 may have the high stress region in front of an end portion along the major axis direction thereof and have the low stress region in front of a longer side along the minor axis direction thereof. Thus, a probability of crack formation in the high stress region of the first pore 120 may be relatively higher than that in the low stress region on the filter 100 with the first pore 120 arranged thereon. Terms of the high stress region and the low stress region are used to compare a relative magnitude of stress and for the sake of convenience in description.

Descriptions about the stress region above may be equally applicable to the second pore 130 and duplicate content will be omitted.

The plurality of first pores 120 and the plurality of second pores 130 may be arranged such that respective high stress regions are separated from each other to the hilt and a maximum pore density is obtained. For example, the end portion along the major axis direction of the plurality of second pores 130 may face the central portion of the longer side of the plurality of first pores 120. For example, the first and second pores 120 and 130 may be alternately arranged, respectively in the first direction and the second direction.

With such an arrangement, the high stress region of the second pore 130 may be separated from the high stress region of the first pore 120 to the hilt. Accordingly, the filter 100 may have a relatively lower probability of crack formation. For example, even when an initial crack is formed on the filter 100, the possibility of crack propagation along the high stress region on the filter 100 may be low.

The filter 100 may be configured to filter biomaterial by using the plurality of pores. The biomaterial may denote various body fluids or solution materials which exist inside animals, including human beings, and plants. For example, the biomaterial may include blood. Blood is composed of plasma, a liquid component, and various cells such as red blood cells, white blood cells, and platelets. For example, the filter 100 may be used to filter white blood cells, which have a relatively larger volume in the blood, red blood cells, or platelets. For example, a separate white blood cell may be utilized in an autologous cytotherapy and an induced pluripotent system cell (iPS). For example, separate white blood cells may be used in the autologous cytotherapy in which the white blood cells of a patient having a smaller number of white blood cells in blood are selectively separated, reproduced via a cell division in in-vitro environment, and put back into the patient. In addition, for example, cells including nuclei among separated cells such as white blood cells may be transformed to the iPS by using a difference between a culture solution and the environment.

Referring to FIG. 4, average sizes of the red blood cell and the white blood cell existing in the human blood are illustrated. The red blood cell has a long, elliptical shape and its length in the major axis direction is about 5 µm to about 7 µm. The length in the minor axis direction is shorter than that and is about 3 µm to about 5 µm. The platelet is smaller than the red blood cell and its diameter is about 3 µm to about 5 µm. The white blood cell is largely divided into five kinds. The white blood cell (leukocyte) is divided into a neutrophil, a lymphocyte, a monocyte, an eosinophil, and a basophil. Each kind of the white blood cell has a somewhat different size, but most of white blood cells have circular shapes and larger sizes than the red blood cell. The white blood cell has an approximate diameter of about 7 µm to about 15 µm and the lymphocyte, the smallest among white blood cell components, has a diameter of about 7 µm to about 10 µm.

The filter 100, which is to filter the white blood cell from the red blood cell and the platelet, and to concentrate the white blood cell, may have a pore size, for example, which may not let the lymphocyte pass therethrough but may let the red blood cell pass therethrough.

For example, the lengths in the minor axis direction of the pores 120 and 130 may be approximately about 4 µM to about 7 µm. The lengths in the minor axis direction of the pores 120 and 130 may be about 5 µm to about 6 µm to enhance the filtering performance while preventing a possibility of partially distorted white blood cells from passing therethrough.

For example, the length in the major axis direction of the pores 120 and 130 may be approximately about 10 µm to about 20 µm. The length in the major axis direction of the pores 120 and 130 may be approximately about 17 µm to about 18 µm, to enhance the filtering performance while preventing a possibility that partially distorted white blood cells may pass therethrough.

For example, the shortest distance between the first pore 120 and the second pore 130 may be approximately about 4 µm to about 7 µm. The shortest distance between the first pore 120 and the second pore 130 may be approximately about 5 µm to about 6 µm to secure sufficient durability to prevent cracks and to increase the pore density of the first and second pores 120 and 130.

The filter 100 may have a high area ratio of the plurality of pores over the filter to sufficiently secure the filtering speed. For example, the area ratio of the plurality of pores on the filter 100 with the plurality of pores distributed thereon may be more than or equal to about 30%.

Referring to FIG. 5, the first and second pores 120 and 130 may have various shapes as long as their shapes are longish. For example, the first and second pores 120 and 130 may have elliptical shapes. For example, the first and second pores 120 and 130 may have a cross-sectional shape of a capsule. The elliptical shape may denote the cross-sectional shape of the capsule. For example, the first and second pores 120 and 130 may have a hexagonal shape which is longish in one direction.

FIG. 6 is a plan view of a filter according to a first comparative embodiment. FIG. 7 is a diagram illustrating a stress simulation result of the filter of FIG. 6.

Referring to FIGS. 6 and 7, the filter according to the first comparative embodiment may have the plurality of pores arranged such that high stress regions are close to each other on the filter. For example, the filter according to this embodiment has the plurality of pores arranged such that major axes are in parallel with each other along the first direction. In addition, the filter according to this embodiment may have the plurality of pores arranged in parallel with each other along the second direction. Thus, high stress regions of pores may be overlapped. Accordingly, when an initial crack occurs in the high stress region, the initial crack may propagate along the first direction and this may decrease the function of the filter.

In addition, the initial crack may propagate along the second direction. The reason is that low stress regions between pores are closely connected and furthermore, they are linearly connected along the second direction.

Referring to FIG. 7, a result of von Mises stress simulation of the filter having the pore arrangement according to FIG. 6 is illustrated.

The von Mises stress simulation is one of simulations to identify an occurrence possibility of a fracture including cracks on the filter surface. It may identify a stress level of the filter per time by applying pressure in a three-dimensional space with a consideration of filter characteristics.

The diagram of FIG. 7 illustrates a result of a simulation in which pressure was applied to a filter which includes silicon material and has a length of approximately about 500 µm, a width of approximately about 500 µm, and a thickness of approximately about 10 µm. The simulation was performed such that when a maximum force of 1 Newton per unit area was applied at the center of the filter with reference to a direction perpendicular to the filter, the pressure would have a Gaussian distribution as the pressure point moves toward edges of the filter. A same condition is presupposed for simulations to be described below.

Referring to FIG. 7, the high level of stress may occur in each pore along the first and second directions at the central portion of the filter to which a high pressure is applied. Thus, when the initial crack occurs, the possibility of crack propagation may be high along the first or second direction.

FIG. 8 is a plan view of a filter according to a second comparative embodiment. FIG. 9 is a diagram illustrating a stress simulation result of the filter of FIG. 8.

Referring to FIGS. 8 and 9, the filter according to the second comparative embodiment may have the plurality of pores arranged such that high stress regions are close to each other. For example, the filter according to this embodiment may have the plurality of pores arranged such that major axes are in parallel with each other along the first direction. In addition, the filter according to this embodiment may have the plurality of pores arranged such that major axes are in parallel with each other along the second direction. Thus, high stress regions of respective pores may be overlapped. Accordingly, when the initial crack occurs in the high stress region, the initial crack may propagate along the first and second directions. In addition, since the propagation possibility, in the first and second directions is almost same, the crack may propagate through between high stress regions. In this case, since the crack may two-dimensionally propagate, the function of the filter may be relatively, more largely damaged.

Referring to FIG. 9, the high level of stress may occur along the first and second directions of each pore at the central portion of the filter to which a high pressure is applied. In addition, unlike FIG. 8, the level of stress may form a circular shape, based on central points in which the first direction and the second direction intersect with each other. Thus, the crack may two-dimensionally propagate on the filter.

FIG. 10 is a plan view of a filter 200 according to an embodiment. FIG. 11 is a diagram illustrating a stress simulation result of the filter 200 of FIG. 10.

Referring to FIGS. 10 and 11, the filter 200 may have each of the plurality of first pores 220 and each of the plurality of second pores 230 alternately arranged, respectively in the first and second directions. For example, end portions along the major axis direction of the plurality of second pores 230 may face central portions of longer sides of the plurality of first pores 220. For example, end portions along the major axis direction of the plurality of first pores 220 may face central portions of longer sides or regions adjacent thereto of the plurality of second pores 230. For example, the plurality of first pores 220 and the plurality of second pores 230 may be arranged to intersect with each other.

The filter 200 according to the embodiment may have high stress regions of the plurality of first pores 220 and those of the plurality of second pores 230 arranged not to contact each other, and thus, the occurrence probability and the propagation probability of the crack has been reduced.

The plurality of first pores 220 and the plurality of second pores 230 may have same shapes. The plurality of first pores 220 and the plurality of second pores 230 may have same major axis lengths ($l_{wa}$) and same minor axis lengths ($l_{ha}$). For example, $l_{wa}$ may be approximately about 17 μm and $l_{ha}$ may be approximately about 6 μm.

Referring to FIG. 10, with an arbitrary first pore as a center; a distance to a second pore arranged above may be $d_{a1}$, that to a second pore arranged below may be $d_{a2}$, that to a second pore arranged left may be $d_{a3}$, and that to a second pore arranged right may be $d_{a4}$. For example, the plurality of first pores 220 and the plurality of second pores 230 may be separated from each other at a same distance. For example, the filter 200 may satisfy a relation that $d_{a1}=d_{a2}=d_{a3}=d_{a4}$.

The plurality of first pores 220 and the plurality of second pores 230 may be separated from each other to increase the pore density of pores while sufficient durability is secured. For example, the filter 200 may satisfy a relation that $d_{a1}=d_{a2}=d_{a3}=d_{a4}$=approximately about 5 μm. The filter 200 according to the embodiment may have a pore density of approximately about 34.6%.

Referring to FIG. 11, the stress level may be high only along major axes of the first and second pores 220 and 230 at the central portion of the filter 200 to which a high pressure is applied. The filter 200, unlike filters according to comparative embodiments 1 and 2, may have the stress levels not connected to each other but discretely formed. Thus, the filter 200 according to the embodiment may have the occurrence probability and the propagation probability of the crack which is relatively lower than that of filters according to comparative embodiments 1 and 2.

FIG. 12 is a plan view of a filter 300 according to another embodiment. FIG. 11 is a diagram illustrating a stress simulation result of the filter 300 of FIG. 12.

Referring to FIGS. 12 and 13, the plurality of second pores 330 may have a pair of first pores 320 respectively arranged on one side and the other side thereof along the first direction. End portions along the major axis direction of the plurality of second pores 330 may face central portions of longer sides of the plurality of first pores 320. For example, the pair of first pores 320 may be arranged along the first direction between adjacent second pores 330.

In addition, the plurality of second pores 330 may respectively have the pair of first pores 320 arranged on, one side and the other side thereof along the second direction. For example, the pair of first pores 320 may be arranged along the second direction between adjacent second pores 330.

The filter 300 according to an embodiment may have an arrangement such that the high stress regions of the plurality of first pores 320 and those of the plurality of second pores 330 are not in contact with each other, and thus, the occurrence probability and the propagation probability of the crack may be reduced. In addition, the pair of first pores 320 may be arranged on each side of the plurality of second pores 320 so as to enhance the pore density of the filter 300.

The plurality of first pores 320 and the plurality of second pores 330 may have same shapes. The plurality of first pores 320 and the plurality of second pores 330 may have same major axis lengths ($l_{wb}$) and same minor axis lengths ($l_{hb}$). For example, $l_{wb}$ may be approximately about 17 μm and $l_{hb}$ may be approximately about 6 μm. With an arbitrary second pore 330 as a basis, distances to adjacent first pores 320 may be $d_{b1}$, $d_{b2}$, $d_{b3}$, and $d_{b4}$. For example, it may be possible that $d_{b1}=d_{b2}=d_{b3}=d_{b4}$. For example, it may be possible that $d_{b1}=d_{b2}=d_{b3}=d_{b4}$=approximately about 5 μm. The pore density of the filter 300 which satisfies such a condition may be approximately about 39.0%.

Referring to FIGS. 12 and 13, at the central portion of the filter 300 to which a high pressure is applied. The stress level may appear high only along major axis directions of the first and second pores 320 and 330. While the pore density of the filter 300 according to the embodiment may be relatively high, the stress level may be relatively higher than that of the filter 200 of FIG. 10 since end portions along the major axis directions of the first and second pores 320 and 330 are relatively closer to each other. However, the filter 300 according to the embodiment may still have a lower stress level than that of the filters according to comparative embodiments 1 and 2 described above, and may still have a lower occurrence probability and propagation probability of the crack.

FIG. 14 is a plan view of a filter 400 according to another embodiment. FIG. 15 is a diagram illustrating a stress simulation result of the filter 400 of FIG. 14.

Referring to FIGS. 14 and 15, one first pore 420 may be arranged on each of one sides and each of the other sides along the first direction of the plurality of second pores 430, and the center line along the major axis direction of the first pore 420 arranged on one side and the center line along the major axis direction of the first pore 420 arranged on the other side may be reciprocally separated from each other in the second direction. For example, with a second pore 431 as a reference, the first pore 421 located on one side in the first direction and a first pore 422 located on the other side in the first direction may be separated from each other along the second direction such that extended lines on respective major axis directions are not overlapped with each other.

The filter 400 according to an embodiment may have the high stress regions of the plurality of first pores 420 and those of the plurality of second pores 430 arranged not to contact with each other, and thus, the occurrence probability and the propagation probability of cracks may be reduced. Furthermore, a disposition, in which centerlines in the major axis direction of respective first pore 420 are separated from each other in the second direction, may further reduce the propagation probability of the crack. According to an embodiment, a case, in which the plurality of first pores 420 are arranged so as to have major axes of first pores 420 be separated from each other, is described as an example; however, it is not limited thereto. For example, For example, the plurality of second pores 430 may be arranged so as to have major axes of second pores 430 be separated from each other.

The plurality of first pores 420 and the plurality of second pores 430 may have same shapes. The plurality of first pores 420 and the plurality of second pores 430 may have same major axis length ($l_{wc}$) and same minor axis length ($l_{hc}$). For example, $l_{wc}$ may be approximately about 18 μm and $l_{hc}$ may be approximately about 6 μm. With an arbitrary second pore 430 as a reference, distances to adjacent first pore 420 may be $d_{c1}$, $d_{c2}$, $d_{c3}$, and $d_{c4}$. For example, distances may be that $d_{d1}=d_{c2}=d_{c3}=d_{c4}$. For example, they may be that $d_{c1}=d_{c2}=d_{c3}=d_{c4}$=approximately about 6 μm.

For example, the pore density of the filter 400 may be approximately about 30.9%.

Referring to FIGS. 14 and 15, at the central portion of the filter 410 to which a high pressure is applied, the high level of stress may appear only along the major axis direction of the first and second pores 420 and 430.

FIG. 16 is a plan view of a filter 500 according to another embodiment. FIG. 17 is a diagram illustrating a stress simulation result with regard to the filter 500 of FIG. 16.

Referring to FIGS. 16 and 17, a plurality of third pores 540 may be arranged between a plurality of first pores 520 and a plurality of second pores 530. Each of the plurality of third pores 540 may have a shape approximately circular, compared with those of the plurality of first pores 520 and the plurality of second pores 530. For example, each of the plurality of third pores 540 may have a circular shape, a square shape, or a rhombus shape. For example, each of the plurality of third pores 540 may have same lengths in first and second directions.

According to an embodiment, the filter 500 may additionally include the plurality of third pores 540 compared to the filter 100 of FIG. 10. However, the filter 500 is not limited thereto. Among various dispositions of first and second pores 520 and 530 in which high stress regions are not overlapped each other; the pore density of the filter 500 may be enhanced by adding third pores 540 into a space between first and second pores 520 and 530.

According to an embodiment, the filter 500 may have the high stress regions of the plurality of first pores 520 and those of the plurality of second pores 530 arranged such that stress regions do not contact with each other, and thus, the occurrence and propagation probability of cracks may be reduced.

The plurality of first pores 520 and the plurality of second pores 530 may have a same shape. The plurality of first pores 520 and the plurality of second pores 530 may have a same major axis length ($l_{wd}$) and a same minor axis length ($l_{hd}$). For example, $l_{wd}$ may be approximately about 18 μm and $l_{hd}$ may be approximately, about 6 μm.

Referring to FIG. 16, with an arbitrary first pore 320 as a basis, distances to adjacent second pores 330 may be $d_{d1}$, $d_{d2}$, $d_{d3}$, and $d_{d4}$. For example, the plurality of first pores 520 and the plurality of second pores 530 may be separated from each other with a same distance. For example, the filter 500 may satisfy a relation that $d_{d1}=d_{d2}=d_{d3}=d_{d4}$. For example, the filter 500 may satisfy a relation that $d_{d1}=d_{d2}=d_{d3}=d_{d4}$=approximately about 6 μm.

With an arbitrary plurality of third pores 540 as a basis, distances to the plurality of first pores 520 and the plurality of second pores 530 may be respectively $d_{d5}$ and $d_{d6}$ along each direction. For example, the filter 500 may satisfy a relation that $d_{d5}=d_{d6}$. For example, the filter 500 may satisfy a relation that $(d_{d5}+d_{d5})=d_{d1}=d_{d2}=d_{d3}=d_{d4}$. For example, the filter 500 may satisfy a relation that $d_{d5}=d_{d6}$=approximately about 3 μm.

The filter 500 may have a pore density of approximately about 39.7% according to an embodiment.

FIG. 18 is a plan view of a filter 600 according to another embodiment.

Referring to FIG. 18, a plurality of first pores 620 and a plurality of second pores 630 may be arranged in the filter 600 n such that respective high stress regions do not directly contact each other. An arrangement of the plurality of first pores 620 and the plurality of second pores 630 in the filter 600 may be combinations of the pores arrangements described above with regard to FIGS. 10 through 17.

FIGS. 19A and 19B are diagrams illustrating a filter structure 800 according to an embodiment.

Referring to FIGS. 19A and 19B, the filter structure 800 may include a filter layer 810 and a support member 820.

The filter layer 810 may include at least one filter according to embodiments described above. The filter layer 810 may include a semiconductor material. For example, the filter layer 810 may include a silicon material.

The support member 820 may support a bottom surface of the filter layer 810. The support member 820 may include an opening H10 to expose the bottom surface of the filter layer 810. For example, the support member 810 may include a plastic material or a glass material.

The filter structure 800 according to this embodiment may be used as a silicon-on-glass (SOG) chip. The filter structure 800 may be manufactured as a SOG substrate. For example, the filter structure 800 may be manufactured by etching the SOG substrate in a semiconductor process.

FIG. 20 is a diagram of a device including a filter according to embodiments described above.

Referring to FIG. 20, the device may include a filter according to embodiments described above, an injection unit injecting the biomaterial to the filter, and a storing unit storing the biomaterial having passed the filter. For example, the injection unit may be a syringe or a cylinder. For example, the storing unit may be a tube or a cylinder. For example, the filter may be arranged at the bottom end of the injection unit. For example, the filter and the support member supporting the filter may be arranged at the bottom end of the injection unit. The injection unit and the storing unit may be connected with each other through a tube.

The filter and the device including the filter according to an embodiment may have a high filtering efficiency. Results of tests performed, using the filter 200 according to FIG. 11, are described below.

TABLE 2

| Kind of Cells | Injected Cells | Collected Cells | Collection Rate (%) |
|---|---|---|---|
| Jurkat | 2.60*E5/mL | 2.52*E5/mL | 96.9 |
| LNCaP | 5.17*E5/mL | 5.17*E5/mL | 100 |

Referring to Table 2, the filtering efficiency of the filter 200 was tested by using a Jurkat cell, a modified cell of T lymphocyte, and an LNCaP, a prostate cancer cell, as a replacement for the white blood cell. A diameter of the Jurkat cell is approximately about 11 μm and that of the LNCaP cell is approximately about 14 μm. 96.9% of injected Jurkat cells were filtered and 100% of the LNCaP cells were filtered.

TABLE 3

| Filtering Method | Number of Filtered White Blood Cells | Filtering Time | Contamination of Red Blood Cells |
| --- | --- | --- | --- |
| Chemical Solution Method of Red Blood Cell | 3.2*E6/mL | 40 minutes | High |
| Ficoll-Paque Separation Method | 2.4*E6/mL | 90 minutes | Low |
| Track-etched Membrane | 3.4*E6/mL | 15 minutes | Low |
| Filter according to First Embodiment | 3.6*E6/mL | 15 minutes | Low |

Table 3 shows the filtering efficiency of the filter 200 in comparison to other methods. In the case of the filter 200, the number of filtered white blood cells is 3.6*E6/ml, which is greater than the number of white blood cells filtered via the other methods. Also, the filtering time when the filter 200 is used is the shortest. Since the filter 200 filters white blood cells with respect to a size difference of the cells, contamination caused by dissolution of red blood cells may not occur.

The filter and the device including the filter may be used in various areas. For example, the filter may be applied to a globule separator or an analyzer of the blood or other body fluid. For example, the filter may be applied to the therapy in which the white blood cell is concentrated, the number of autologous white blood cells is reproduced and used, or to an integrated device for manufacturing stem cells through transformation of blood cells, etc. to the iPS cells. For example, the filter may be used to perform pre-processing of the red blood cell in a device for a molecular analysis on cells in the blood. For example, the filter may be applicable to a device which performs a molecular analysis such as polymerase chain reaction (PCR) after removing contaminated cells such as the red blood cell in a liquid biopsy on tissue, etc. which is obtained via a fine needle aspiration, etc. For example, the filter may be used in a concentration process of cells in a limited space such as an intensive care unit in a hospital, a mobile medical chamber, a bloodmobile, etc. in which an infection possibility due to external germs, etc. needs to be minimized.

It should be understood that the embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

The invention claimed is:

1. A filter comprising a rigid plate comprising a semiconductor material, the plate comprising a plurality of pores arranged two-dimensionally to filter a biomaterial, wherein the plurality of pores comprises:
a plurality of first pores extending in a first direction and having a relatively longer structure in the first direction than in a direction perpendicular to the first direction; and
a plurality of second pores having a relatively long structure in a second direction different from the first direction,
wherein an end portion along a major axis direction of the second pores faces a central portion on a longer side of the first pores;
wherein the shortest distance between the first pores and the second pores is 4 μm to 7 μm; and
wherein the first and second pores have a length in a minor axis direction and a length in a major axis direction, and the length of each of the first and second pores in the major axis direction is 10 μm to 20 μm, and the length of each of the first and second pores in the minor axis direction is 4 μm to 7 μm.

2. The filter of claim 1, wherein the first and second pores are respectively alternately arranged in the first and second directions.

3. The filter of claim 1, wherein the end portion along the major axis direction of the first pores faces the central portion of the longer side of the second pores or an area adjacent thereto.

4. The filter of claim 1, wherein pairs of some of the first pores are respectively arranged in the first direction with a second pore in between each two pairs, the second pore being aligned in the first direction, and pairs of some of the first pores are respectively arranged in the second direction with the second pore in between each two pairs.

5. The filter of claim 1, wherein some of the first pores are respectively arranged in the first direction with a second pore in between each two of the first pores, the second pore being aligned in the first direction, and some of the first pores are respectively misaligned so that major axis directions of the first pores are separated along the second direction.

6. The filter of claim 1, wherein the plurality of pores further comprises a plurality of third pores between the plurality of first pores and the plurality of second pores.

7. The filter of claim 6, wherein the third pores have same length in the first and second directions.

8. The filter of claim 1, wherein the plurality of pores are separated by uniform gaps in the first and second directions.

9. The filter of claim 1, wherein each of the first and second pores has an elliptical shape.

10. The filter of claim 1, wherein the ratio of the length in the major axis direction to the length in the minor axis direction of each of the first and second pores is greater than or equal to about 2.5.

11. The filter of claim 1, wherein a shortest distance between the first pores and the second pores is 5 μm to 6 μm.

12. The filter of claim 1, wherein the ratio of an area of the plurality of pores to an area of the filter is greater than or equal to 30%.

13. The filter of claim 1, wherein the biomaterial comprises blood, and the first and second pores are configured to allow red blood cells in the blood to pass therethrough but not to allow white blood cells in the blood to pass therethrough.

14. The filter of claim 1, wherein a support member is on a bottom surface of the filter to support the filter and comprises at least one opening exposing the bottom surface of the filter.

15. A filter comprising a rigid plate comprising a semiconductor material, the plate comprising a plurality of pores arranged two-dimensionally to filter a biomaterial,
wherein the plurality of pores comprise:
a plurality of first pores extending in a first direction and having a relatively longer structure in the first direction than in a direction perpendicular to the first direction; and
a plurality of second pores having a relatively long structure in a second direction different from the first direction,
wherein the first and second pores are respectively alternately arranged in the first and second directions;
wherein the shortest distance between the first pores and the second pores is 4 μm to 7 μm; and
wherein the first and second pores have a length in a minor axis direction and a length in a major axis direction, and the length of each of the first and second pores in the major axis direction is 10 μm to 20 μm, and the length of each of the first and second pores in the minor axis direction is 4 μm to 7 μm.

16. The filter of claim 15, wherein an end portion along a major axis direction of the first pores faces a central portion of a longer side of the second pores, and/or the end portion along the major axis direction of the second pores faces the central portion of the longer side of the first pores.

17. A device comprising:
the filter of claim 1;
an injection unit injecting the biomaterial into the filter; and
a storing unit storing the biomaterial that passed through the filter.

* * * * *